US006482328B1

(12) United States Patent
Davidson et al.

(10) Patent No.: US 6,482,328 B1
(45) Date of Patent: Nov. 19, 2002

(54) METHOD AND APPARATUS FOR MAGNETICALLY SEPARATING SELECTED PARTICLES, PARTICULARLY BIOLOGICAL CELLS

(76) Inventors: Chaim Davidson, Yishuv Bar Yochai, 13912 D.N. Merom Hagalil (IL); Ofer Klein, Moshav She'ar Yeshuv, 12240 D.N. Gaill Ellon (IL); Ahron Lamish, 19 Hahuia Street, 52255 Fernat Gan (IL)

(*) Notice: Subject to any disclaimer, the term of this patent is extended or adjusted under 35 U.S.C. 154(b) by 0 days.

(21) Appl. No.: 09/700,218

(22) PCT Filed: May 13, 1999

(86) PCT No.: PCT/IL99/00255

§ 371 (c)(1), (2), (4) Date: Nov. 13, 2000

(87) PCT Pub. No.: WO99/59694

PCT Pub. Date: Nov. 25, 1999

(30) Foreign Application Priority Data

May 17, 1998 (IL) ................................................ 124514

(51) Int. Cl.[7] ...................... B01D 35/06; G01N 33/553; B01L 11/00; B03C 1/00

(52) U.S. Cl. .................... 210/695; 210/222; 210/416.1; 210/808; 209/215; 422/44; 435/287.1; 436/526

(58) Field of Search ............................. 210/222, 416.1, 210/695, 704, 705, 710, 808; 209/219, 222, 223.1, 215, 223, 226; 252/62.51 R; 422/44, 101; 435/2, 7.2, 7.21, 287.1; 436/526

(56) References Cited

U.S. PATENT DOCUMENTS 4,710,472 A * 12/1987 Saur et al. .................. 210/222
5,536,475 A * 7/1996 Moubayed .................. 422/101

* cited by examiner

*Primary Examiner*—David A. Reifsnyder
(74) *Attorney, Agent, or Firm*—G. E. Ehrlich Ltd.

(57) ABSTRACT

A method and apparatus for magnetically separating target particles of a selected type from a sample in order to produce a concentration of the target particles in the sample, or a depletion of the sample with respect to the target particles, by producing a sample mixture of the sample with magnetic particles having a selective affinity to magnetically stain the target particles; producing a flow of a buffer liquid through a tube which includes an inlet connectable to a source of buffer liquid, and an outlet for the buffer liquid; after a flow of the buffer liquid has been produced through the tube, introducing the sample mixture into the buffer liquid flowing through the tube such that the buffer liquid forms a continuous liquid carrier for the sample mixture as both are fed through the tube; and applying a magnetic field across the tube at a magnetizing station therein to cause the magnetically-stained target particles to be separated and retained in the buffer liquid within the tube at the magnetizing station.

22 Claims, 6 Drawing Sheets

METHOD AND APPARATUS FOR MAGNETICALLY SEPARATING SELECTED PARTICLES, PARTICULARLY BIOLOGICAL CELLS

FIELD AND BACKGROUND OF THE INVENTION

The present invention relates to a method and apparatus for magnetically separating particles of a selected type (hereinafter called "target particles") from a sample in order to produce a concentration of the target particles in the sample, and or a depletion of the sample with respect to the target particles. The invention is particularly useful for magnetically separating biological cells of a selected type, e.g., a selected type of lymphocyte cell in a blood sample, and is therefore described below especially with respect to such applications.

A large number of applications involving the magnetic separation of biological cells are described in the literature, for example in U.S. Pat. No. 4,710,472 and the many publications cited therein, which are hereby incorporated by reference. Many such applications require not only the separation of one or more specific types of cells (hereinafter called "target cells"), but also the maintenance of the quality of the cell membranes in the target cells, and/or in the untargetted cells. Thus, in a positive selection process, the target cells are separated from a sample for examination or use for research, diagnostic or clinical purposes; whereas in a depletion process, the sample is depleted of the target cells for examination or use of the untargetted cells. The separation of target cells from the untargetted cells, and the maintenance of the membranes of both the target cells and untargetted cells, are particularly important in research presently being conducted with lymphocyte populations and their role in the early detection of cancer.

One technique in present use for the separation of biological cells utilizes the MiniMACS Separation Columns (Miltenyi Biotec GmbH). This technique uses paramagnetic microbeads which are extremely small, about 50 nm in diameter, i.e., about one milion times smaller in volume than that of eukatyotic cells, compared to the size of a virus. Such magnetic microbeads are produced with selective affinities for certain cells, i.e., the target cells, such that they magnetically label or stain the target cells. The sample is introduced into a magnetic separation column including a liquid-pervious magnetic body, e.g., steel wool or mesh, and a magnetic field is applied across the column such that the magnetically stained cells are retained in the liquid-pervious magnetic body of the column, while the unstained cells pass through the column. In this known process, however, it was found that the membranes of the cells are excessively damaged by the liquid-pervious magnetic body, which reduces the effectiveness of the technique for research or clinical purposes.

OBJECTS AND BRIEF SUMMARY OF THE INVENTION

An object of the present invention is to provide a method of magnetically separating target particles of a selected type from a sample in a manner which causes less damage to the membrane than the above described known technique. Another object of the present invention is to provide apparatus for magnetically separating target particles in accordance with the novel method.

According to one aspect of the present invention, there is provided a method of magnetically separating target particles of a selected type from a sample in order to produce a concentration of the target particles in the sample, or a depletion of the sample with respect to the target particles, comprising: producing a sample mixture of the sample with magnetic particles having a selective affinity to magnetically stain the target particles; producing a flow of a buffer liquid through a tube which includes an inlet connectable to a source of buffer liquid, and an outlet for the buffer liquid; after a flow of the buffer liquid has been produced through the tube, introducing the sample mixture into the buffer liquid flowing through the tube such that the buffer liquid forms a continuous liquid carrier for the sample mixture as both are fed through the tube; and applying a magnetic field across the tube at a magnetizing station therein to cause the magnetically-stained target particles to be separated and retained in the buffer liquid within the tube at the magnetizing station.

Such a method is particularly useful in a depletion process, wherein a sample depleted of the target particles is to be produced for diagnostic examination, research, or clinical purposes.

According to further features in the described preferred embodiments, the magnetically-stained target particles in the sample mixture, which are separated and retained in the buffer liquid within the tube at the magnetizing station, are subsequently removed from the tube by terminating the introduction of the sample mixture into the buffer liquid and the application of the magnetic field across the tube, while the buffer liquid is fed through the tube to flush out the magnetically-stained target particles with the buffer liquid. Such a method is particularly useful in a positive selection process, wherein the target particles are to be separated and used for diagnostic examination, research or clinical purposes.

According to another aspect of the present invention, there is provided apparatus for magnetically separating target particles of a selected type from a sample in order to produce a concentration of the target particles in the sample, or a depletion of the sample with respect to the target particles, comprising: a buffer liquid supply; a tube for feeding a buffer liquid from the buffer liquid supply at an inlet end of the tube to an outlet end of the tube; a sample container for containing a mixture of the sample with magnetic particles having a selective affinity to magnetically stain the target particles; a feed tube connecting the container to the inlet end of the tube to enable feeding the mixture through the tube after a flow of buffer liquid has been produced therein, such that the buffer liquid forms a continuous liquid carrier for the magnetically-stained target particles of the mixture fed through the tube; magnetic field producing means for producing a magnetic field across the tube at a magnetizing station therein to cause the magnetically-stained target particles to be separated and retained in the buffer liquid within the tube at the magnetizing station; and a container located at the outlet end of the tube for receiving the buffer liquid and the sample depleted of the target particles.

Where the apparatus is to be used in a positive selection process, the apparatus further comprises a second container which can be located at the outlet end of the tube in place of the first-mentioned container; in addition, the application of the magnetic field, and the inputting of the mixture into the buffer liquid, are both terminated to cause the buffer liquid fed through the tube to flush out the magnetically-stained target particles into the second container.

Such a method and apparatus have been found to enable the separation of selected types of particles, (target particles), particularly biological cells (target cells), without causing undue damage to either the target particles or the untargetted particles. Thus, the buffer liquid, which forms a continuous liquid carrier for both the target particles and the untargetted particles, produces a constant liquid volume which physically supports both types of particles (or cells) during both phases of the process, thereby minimizing damage to both types of particles during both phases.

While the method and apparatus of the present invention are particularly useful for separating selected types of biological cells, such method and apparatus may also be used for separating other types of particles, e.g., selected proteins. Also, while the described method and apparatus preferable use the commercially-available magnetic microbeads, it will be appreciated that other magnetic particles having a selective affinity for the target particles may be used to magnetically stain or label the target particles.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
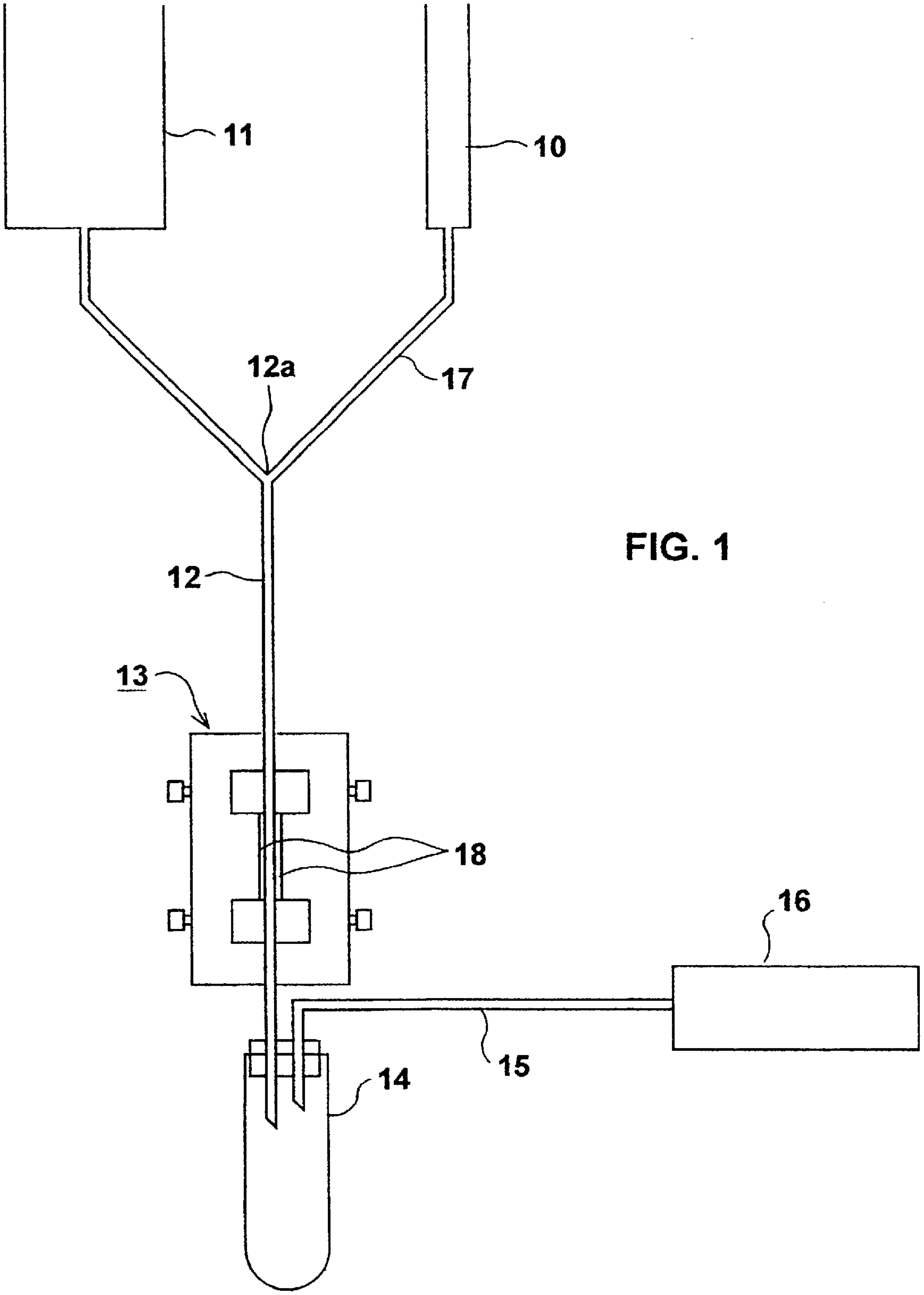
FIG. 1 schematically illustrates the basic elements of one form of apparatus constructed in accordance with the present invention.

The apparatus illustrated in FIG. 1 is particularly useful for magnetically separating certain types of target cells, such as lymphocytes, red blood cells, and/or macrophages, from a blood sample.

The illustrated apparatus includes a sample container 10 to contain the blood sample. Before or after the blood sample is introduced into container 10, it is mixed with magnetic particles, preferably the commercially-available magnetic microbeads, having a selective affinity to magnetically stain or label the target cells in the blood sample within container 10.

The apparatus further includes another container 11 which serves as a supply of a buffer liquid to be used in the magnetic separation process. The buffer liquid in container 11 may be any of the commercially-available buffer liquids, such as normal saline solution, PBS, and the like.

The apparatus illustrated in FIG. 1 further includes a feed tube 12 for feeding the buffer liquid from the buffer container 11 through a magnetizing station 13 to a receiving container 14. In the embodiment of FIG. 1 the feeding of the buffer liquid via feed tube 12 is effected by gravity and a vacuum. For this purpose, the two supply containers 10 and 11 are located above the receiving container 14; and the receiving container 14 includes a vacuum tube 15 communicating at one end with the interior of the receiving container, and at the opposite end with a vacuum source 16.

The blood sample within the sample container 10 includes the magnetically-stained target cells as well as the non-targetted cells. The blood sample is introduced via line 17 into an input port 12*a* in the feed tube 12 at a location upstream of the magnetizing station 13. However, before the sample is introduced into the feed tube 12, the feed tube is first filled with degassed buffer liquid from container 1, and a predetermined flow rate is effected. The flow rate is preferably less than one drop per second; a preferred flow rate is 6–8 drops per minute. Presetting the flow rate may be effected by controlling the vacuum source 16, or by controlling one or more valves as will be described more particularly below with respect to FIG. 2.

The buffer liquid from container 11 thus serves as a continuous liquid carrier for the magnetically-stained target cells and non-target cells in the blood sample introduced from container 10 via the input port 12*a,* as both the buffer liquid and the mixture, including the target cells and non-targetted cells therein, flow via the feed tube 12 through the magnetizing station 13. Magnets 18 at the magnetizing station 13 apply a magnetic field across the feed tube 12 sufficient to separate and retain the magnetically-stained target cells within the buffer liquid at the magnetizing station 13 as the buffer liquid, with the non-magnetized cells and other constituents of the blood sample, flows through the output end of the feed tube 12 into the receiving container 14. The receiving container 14 thus receives the buffer liquid together with the non-targetted cells of the blood sample, since the magnetically-stained target cells of the blood sample (including the magnetic particles mixed therein) are held in stasis by the magnetic flux produced by the magnets 18 in the magnetizing station 13.

The contents of the receiving container 14 thus constitute the results of a depletion process performed on the original sample since these contents include all the original constituents of the sample except for the magnetically-stained target cells (and the magnetic particles added to the original sample in container 10) which are separated and retained in the magnetizing station 13. Accordingly, the contents of container 14 may be examined or used for diagnostic, research, or clinical purposes in the same manner as when using the results of any other corresponding depletion process performed on the original sample.

If it is also desired to perform a positive selection process on the original sample (i.e., to use the separated target cells for diagnostic, research, or clinical purposes), this may be done by: (a) continuing to feed the buffer liquid through tube 12; (b) terminating the supply of the mixture from the sample container 10 and the application of the magnetic field at the magnetizing station 13; and (c) replacing the receiving container 14 with another receiving container (not shown) to receive the target cells which are flushed-out by the buffer liquid fed through the feed tube 12. Generally, it would be preferable, after terminating the introduction of the sample from the sample container 10, to delay for a short time the termination of the application of the magnetic field at the magnetizing station 13 and the switch-over of the two containers, to enable the buffer liquid to rinse-out the magnetically-stained target particles retained in the magnetizing station 13 before such particles are flushed-out to the second receiving container.

Magnets 18 at the magnetizing station 13 may be permanent magnets which can be physically removed or moved away from the magnetizing station when flushing out the magnetically-separated target cells. Alternatively, these magnets 18 may be electromagnets electrically energized via connectors 19 (FIG. 2) during the magnetic-separation phase, and electrically deenergized during the flushing-out phase.

It will be seen that the buffer liquid supplied from the buffer container 11 provides a constant and continuous fluid volume, and thereby forms a continuous liquid carrier for all the constituents of the sample mixture supplied from the sample container 10. This is true both during the initial depletion stage, wherein the original sample depleted of the target cells is received within container 14, and also during the positive selection stage, wherein the target cells separated and retained in the magnetizing station 13 are flushed out by the buffer liquid into another receiving container. The buffer liquid thus continuously supports both the target cells and the non-targetted cells during both phases of the separation process such as to substantially decrease the possibility of damage or rupture of the cell membranes, as compared to the conventional MiniMACS process described above. In addition, and as will be further described below, the method illustrated in FIG. 1 is highly susceptible to automation to provide greater through-put capabilities and improved efficiency in the separation process.

Following is one example of using the apparatus and method described above with respect to FIG. 1 for magnetically separating selected target cells from a blood sample:

A mixed lymphocyte sample was obtained from a quantity of normal, healthy blood using a normal ficoll gradient. This sample was split into two groups: control and experimental. Commercially-available CD19 magnetic Microbeads (supplied by Miltenyi Biotec GmbH) were added to the experimental lymphocytes for the purpose of tagging only B cells in the sample. After staining with the CD19 microbeads, the cells were rinsed twice with PBS.

The separation device was prepared by filling and rinsing the feed tube 12 with degassed buffer from the buffer reservoir. Throughout the separation, the system remains filled with the degassed buffer.

The stained lymphocyte mixture was introduced into the system by way of a 1 ml. syringe (w/o the plunger) with a 0.4×13 needle inserted into a "piggyback site" in the tubing. The vacuum system maintained a steady flow rate of 6 drops per minute. After all the stained mixture had entered the system, the needle was removed and the system left to run until an additional 400 $\mu$l of buffer had flowed through the separation system. Flow was halted. The receiving tube was removed, labeled "A", and replaced with a second tube.

The magnetic field was discontinued; flow was restored; and the line was flushed with 500 $\mu$l of buffer liquid. Flow was again halted, and this second tube was removed and labeled "B".

Cells from the control group and tubes "A" and "B" were examined in a double blind condition with a light microscope for membrane condition and cell counts using a hemocytometer.

There was no change in cell quality between the control and the experimental samples. Normally, B cells comprise 8–11% of the total lymphocyte population. Results of this separation yielded 8.8% B cells, demonstrating the ability to isolate a specific population with no change in the cell quality.

Utilizing CD19 microbeads (Miltenyi Biotec GmbH) to stain for B Lymphocytes, would be expected to produce a harvest of approximately 10% from the total lymphocyte population. The actual results, as examined by light microscope, CellScan, and FACS, were as follows:

1. A harvest was produced ranging from 8.8% to 11.1%. FACS analysis of these cells revealed a 97% pure population of desired cells.

2. The membrane quality was unaffected by the process. This was verified by both light microscope and CellScan examination.

3. The non-stained lymphocyte populations (non-targetted cells) were expected to contain approximately 95% T Lymphocytes and comprise approximately 90% of the total lymphocyte population. FACS analysis of these cells revealed an average of 93% pure T Lymphocyte populations. Microscopic examination confirmed that these T Lymphocytes comprised an average of 90% of the total lymphocyte population.

In the above-described example, the magnetic field was produced by permanent magnets of neodymium; the tubing was 0.80 mm infusion tubing; and the buffer liquid was of the following composition:

15.00 ml total buffer

Figure 2:
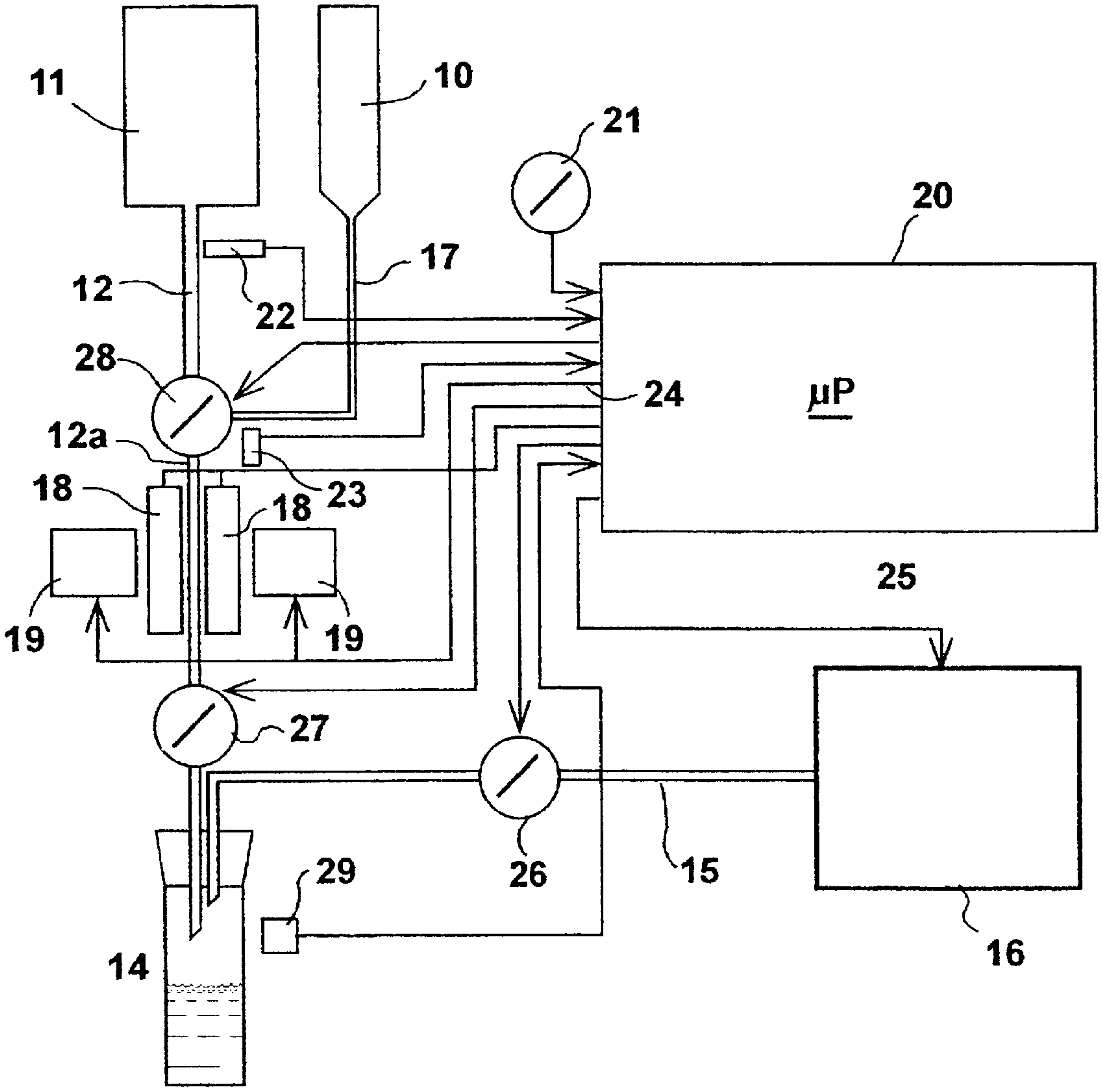
FIG. 2 schematically illustrates a system including apparatus similar to that of FIG. 1 and the main controls therefor.

FIG. 2 schematically illustrates the basic system of FIG. 1 but equipped with the main controls for automating the operation of the system.

Thus, the system illustrated in FIG. 2 includes a microprocessor controller, generally designated 20, for controlling the overall operation of the system. The inputs to controller 20 include a flow selector 21 for presetting the flow rate of feed of the buffer liquid from the buffer container 11; an air bubble sensor 22 for sensing the presence of air bubbles in the buffer feed tube 12; and an air bubble sensor 23 for sensing the presence of air bubbles in the sample feed tube 17. These sensors protect the integrity of the constant fluid level by shutting down fluid flow (sensor 22 will close valve 27, and sensor 23 will close valve 28) if an air bubble is detected. Controller 20 also includes an input from a flow rate sensor 29 for sensing the flow into container 14.

Controller 20 in turn controls the electromagnets 18 at the magnetizing station 13 via line 24 connected to their connectors 19, the vacuum source 16 via line 25 and/or a vacuum valve 26, the feed rate of the buffer liquid via valve 27 in the feed line 12, and the feed rate of the sample via valve 28 in the sample line 17.

FIGS. 3–6 illustrate a variation in the construction of the magnetic unit in the magnetizing station 13 to enable the magnetizing station to occupy a substantially longer flow-path of the buffer liquid carrying the sample, and thereby to increase the throughput and/or efficiency of the overall separation process. Thus, whereas in the apparatus illustrated in FIGS. 1 and 2, the magnetizing station 13 occupies a straight length of the feed tube 12, in FIG. 3 the magnetizing station, therein designated 30, is constructed to occupy an elongated, serpentine length of the feed tube 12.

Figure 4:
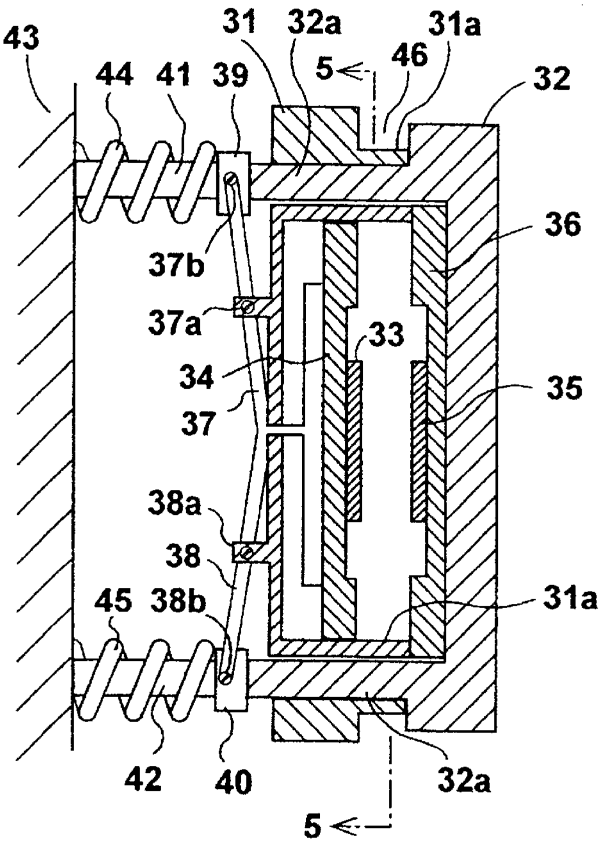
FIG. 4 is a sectional view along line 4—4of FIG. 3.

As shown particularly in FIG. 4, the magnetizing station 30 includes a back mounting plate 31 and a front mounting plate 32 assembled together by pins 32*a* in plate 32 received with a friction fit in apertured posts 31*a* in plate 31. The front mounting plate 31 mounts a plurality of permanent magnets 33 each carried by a magnetizable core element 34; and similarly, the back mounting plate 32 mounts a plurality of permanent magnets 35 each carried by a magnetizable core element 36.

The permanent magnets 33 and 35 are aligned with each other, and the magnetizable core elements 34 and 36 are aligned with each other, so that they define two closed magnetic circuits, one including air gaps $AG_1$, $AG_2$, and the other including air gaps $AG_1$, $AG_3$. The feed tube 12 passes through all three air gaps $AG_1$–$AG_3$, such that the magnetic field produced by the permanent magnets is effective over a substantial length of the feed tube.

The back mounting plate 31 is movably mounted by a pair of rocker arms 37, 38. Each rocker arm includes a pivotal mounting 37*a*, 38*a* to the back mounting plate 31, and another pivotal mounting 37*b*, 38*b* to a collar 39, 40 slidably received on pins 41, 42 projecting from a supporting surface 42. Collar 39 is slideably received on the upper pin 41, and collar 40 is slideably received on the lower pin 42 fixed to the supporting surface 43 below pin 41. The two collars 39, 40 are biassed outwardly by coiled springs 44, 45 on their respective pins 41, 43.

Figure 5:
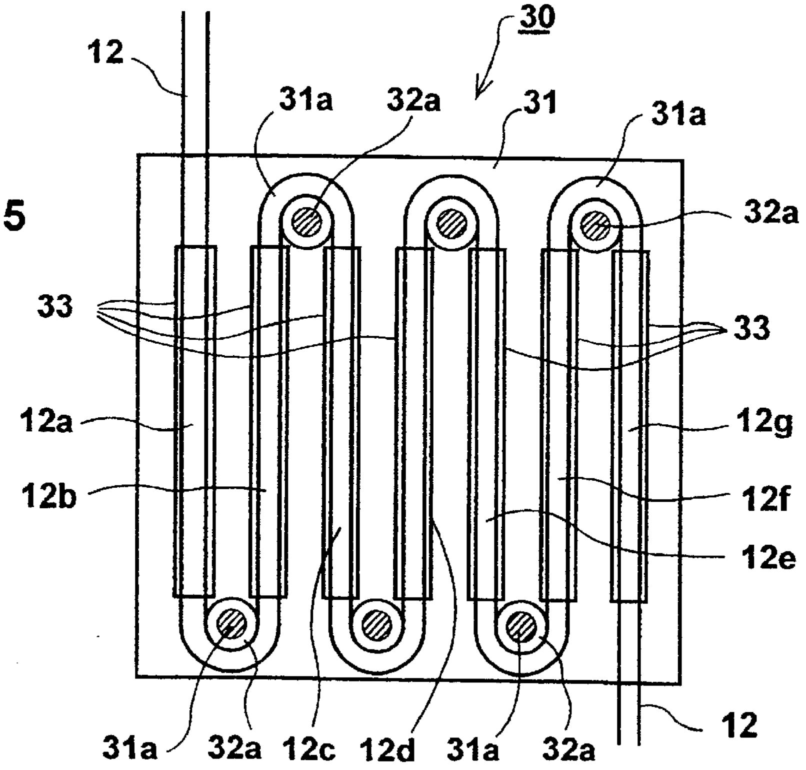
FIG. 5 is a sectional view along line 5—5 of FIG. 4.

As shown in FIG. 5, the back plate 31 includes three apertured posts 31*a* at the upper end, and three such posts at the lower end in staggered relationship with respect to the posts at the upper end. The pins 32*a* in the front mounting plate 32 are correspondingly arranged so as to be received within the apertured posts 31*a* in plate 31. Thus, when the front plate 32 is removed, the feed tube 12 may be wound around the upper and lower posts 31*a* of the back plate 31 in a serpentine fashion (FIG. 5), to produce downwardly-extending and upwardly-extending stretches 12*a*–*g*. The last downwardly-extending stretch 12*g* is connected to the receiving container 14 in FIG. 3.

Figure 6:
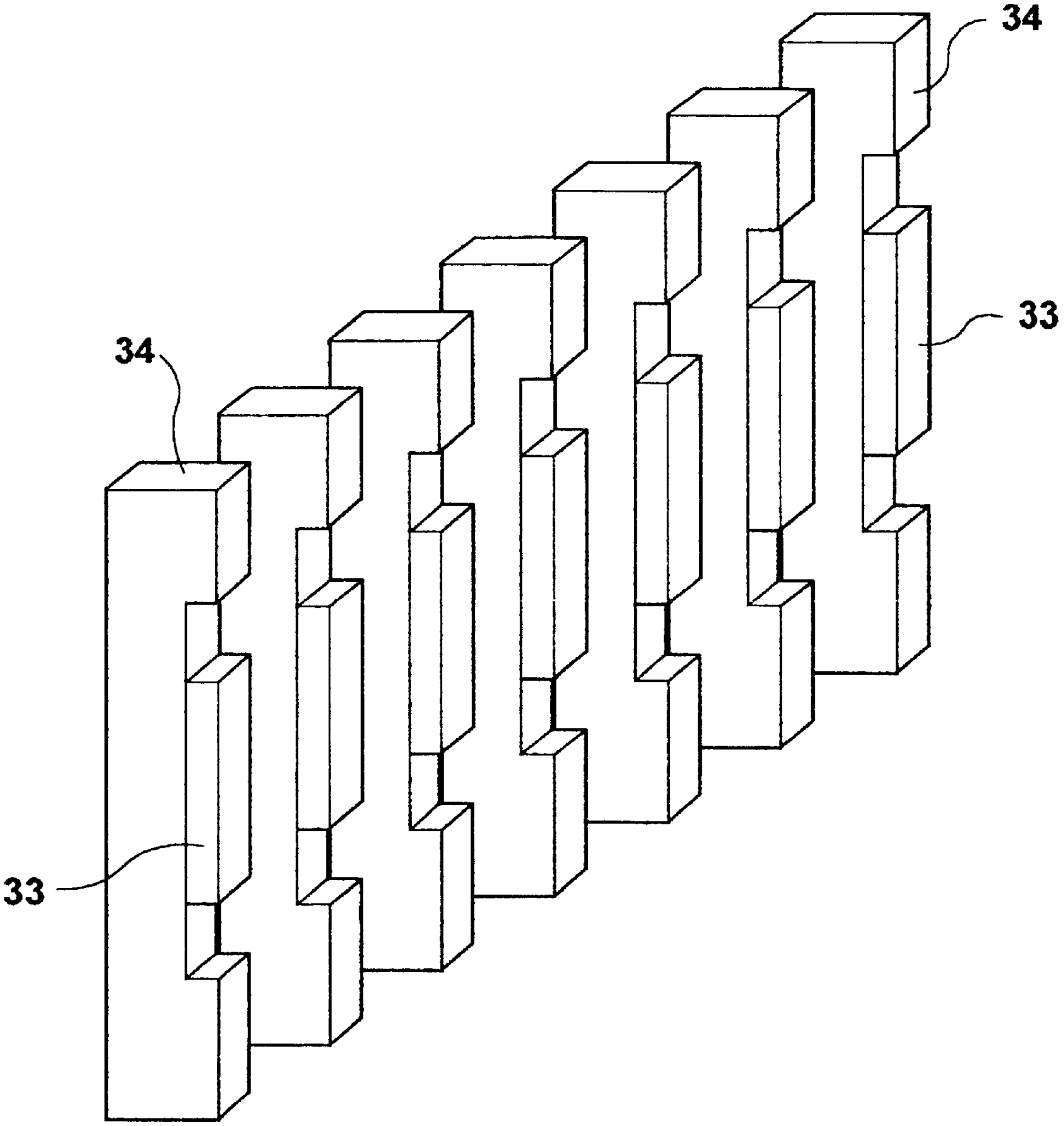
FIG. 6 is an exploded three-dimensional view illustrating the magnet holders, and their corresponding magnets, at one side of the magnetizing station in the apparatus of FIGS. 3–5.

As shown in FIG. 6, there is one magnet 33, for each stretch 12*a*–12*g* of the feed tube. Since the illustrated example shows seven such stretches, FIG. 6 illustrates seven such magnets 33 and their respective core elements 34. There would be a corresponding number of magnets 35 and core elements 36 carried by the front plate 32, with the magnets 35 of the front plate aligned with the magnets 33 of the back plate. As noted above, each pair of magnets and core elements define three air gaps ($AG_1$–$AG_3$, FIG. 4) for each stretch 12*a*–12*g* of the feed tube, such that the magnetic field in the magnetizing station is effective over a considerable length of the feed tube.

Pins 32*a* of the front plate 32, of the same number and arrangement as the posts 32*a* so as to be received within those posts when applying the front plate 35 to the back plate 31, are dimensioned to produce a friction fit when the pins are received within the posts. Posts 31 are also dimensioned to define a space, shown at 46 (FIG. 4), between the magnets 33, 35 carried by the two plates 31, 32 for receiving the respective stretch 12*a*–12*g* of the feed tube 12.

After the feed tube has been applied in serpentine fashion over the apertured posts 31*a* in the back plate 31, the front plate 32 is applied by inserting the pins 32*a* through the posts 31*a*. When the pins 32*a* are received within the posts 31*a*, the pins engage the collars 39, 40, moving them towards the fixed surface 43 against springs 44, 45. The back plate 31 is thus moved by rocker arms 37, 38 towards the front plate 37, to thereby firmly sandwich the respective stretches of the feed tube 12 between the two groups of magnets 33, 35.

Figure 3:
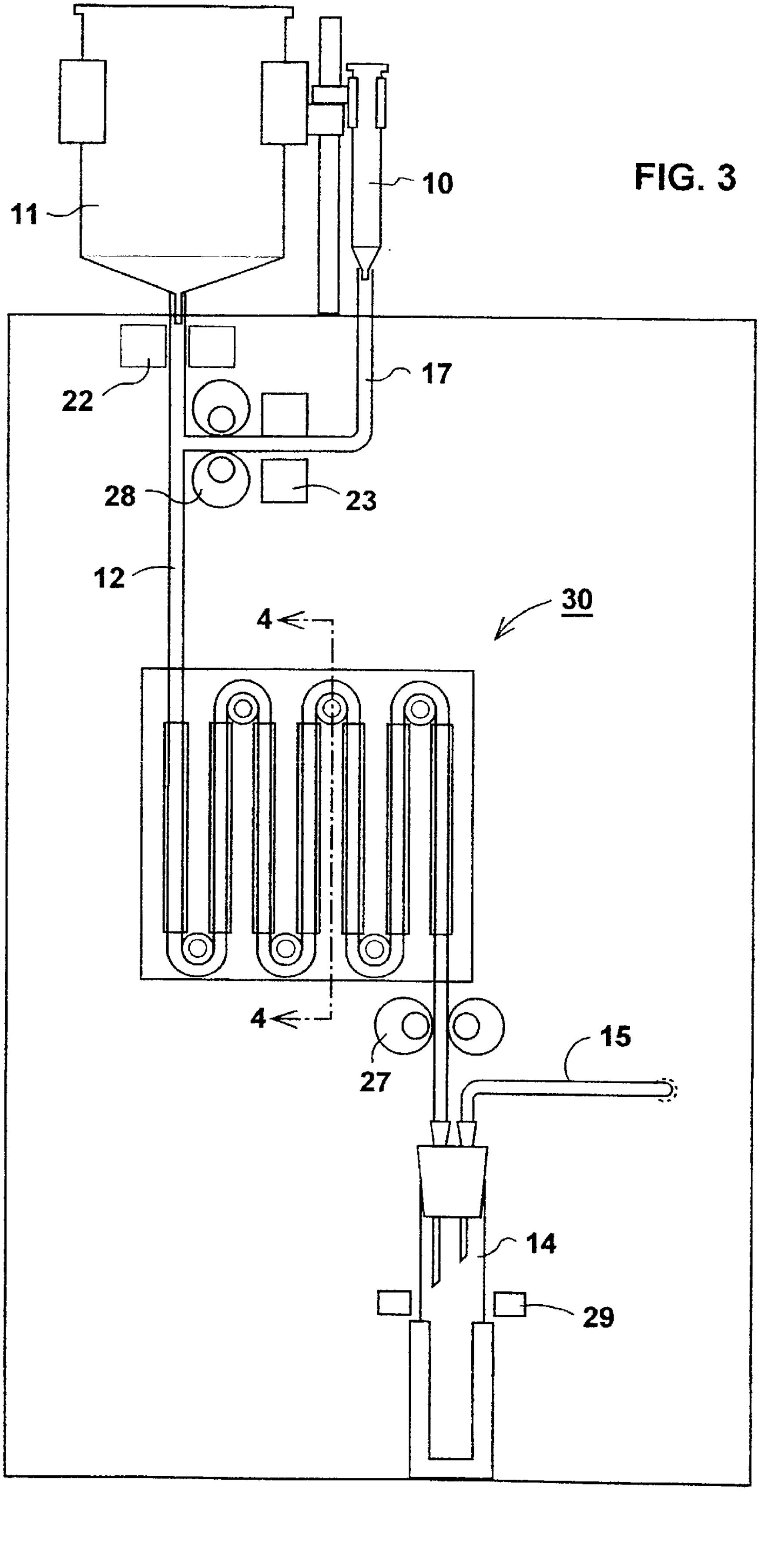
FIG. 3 illustrates the basic elements of a second form of apparatus constructed in accordance with the present invention.
Figure 7:
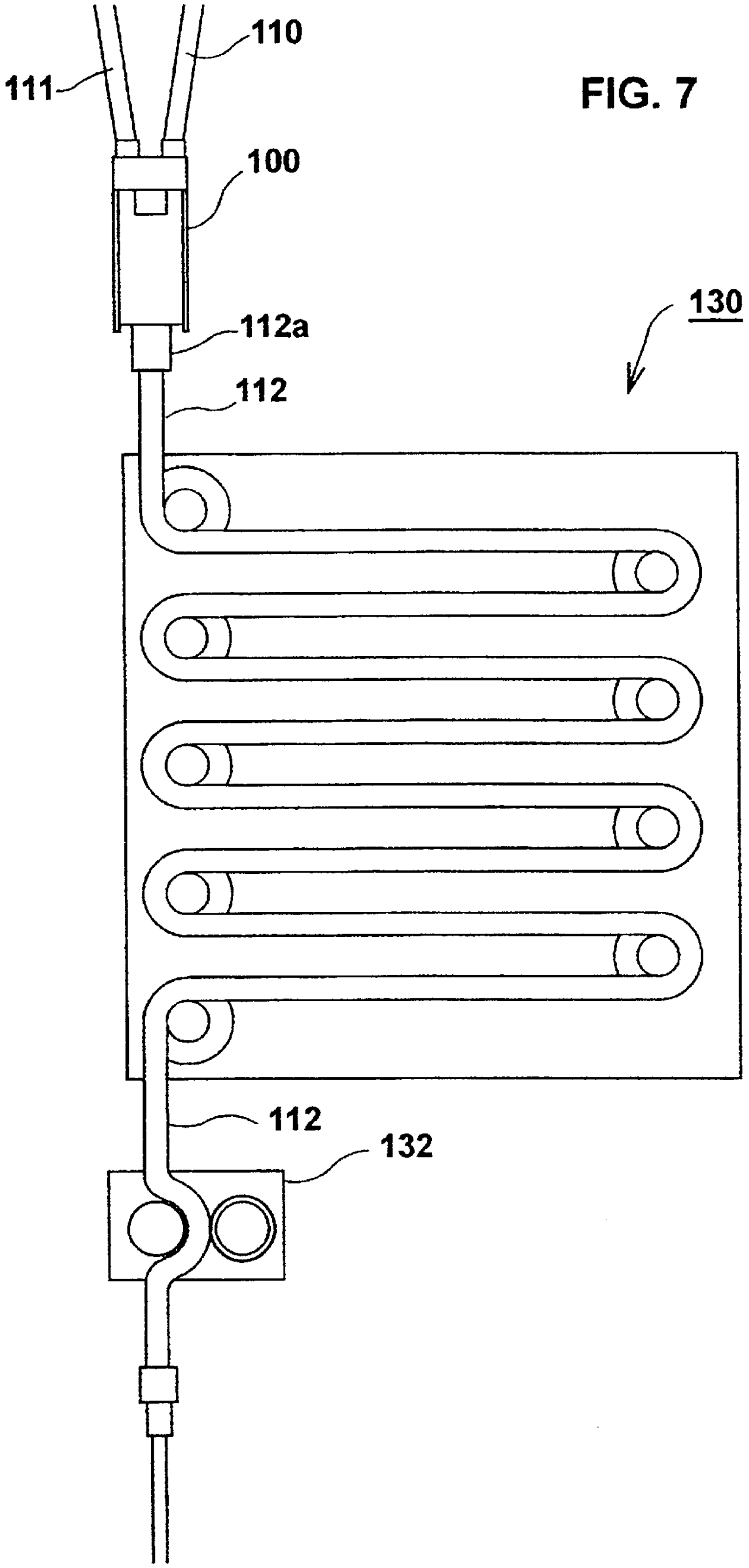
FIG. 7 illustrates another apparatus constructed in accordance with the invention.

FIG. 7 illustrates an apparatus similarto that of FIG. 3, except that the apparatus of FIG. 7 further includes a mixing chamber 100 at the input port 112*a* of the feed tube 112 for pre-mixing the sample mixture applied via inlet tube 110, and the buffer liquid applied via inlet 111, before being fed, via tube 112, to the magnetizing station 130. The apparatus in FIG. 7 further includes a pump 132, such as a peristaltic pump, in the outlet end of tube 112 for controlling the feeding of the liquid therefrom into the receiving container (14, FIG. 3).

In all the above-described embodiments, the magnetic field can be controlled according to the particular application to produce a predetermined field intensity. For this purpose, the magnetic air gap can be changed when using permanent magnets: and when using electromagnets, the current can be varied, e.g., via microprocessor 20 in FIG. 2.

While the invention has been described above with respect to selected target cells from a blood sample, it will be appreciated that the invention could be used in many other applications for the selection of other target particles from a body, such as selected proteins, or other types of particles. Also, while the use of magnetic microbeads is preferred, it will be appreciated that other magnetic particles may be used in the process. Further, other sensors, such as for radioactivity, conductivity, etc. can be included. Many other variations, modifications and applications of the invention will be apparent.

What is claimed is:

1. A method of magnetically separating target particles of a selected type from a sample in order to produce a concentration of the target particles in the sample, or a depletion of the sample with respect to the target particles, comprising:

producing a sample mixture of said sample with magnetic particles having a selective affinity to magnetically stain said target particles;

producing a flow of a buffer liquid through a tube which includes an inlet connectable to a source of buffer liquid, and an outlet for the buffer liquid;

after a flow of said buffer liquid has been produced through said tube, introducing said sample mixture into the buffer liquid flowing through said tube such that the buffer liquid forms a continuous liquid carrier for said sample mixture as both are fed through said tube;

and applying a magnetic field across said tube at a magnetizing station therein to cause the magnetically-stained target particles to be separated and retained in the buffer liquid within the tube at the magnetizing station.

2. The method according to claim 1, wherein said sample mixture is introduced into said buffer liquid at a location between the inlet end of the tube and said magnetizing station.

3. The method according to claim 1, wherein the target particles which are magnetically-stained by the magnetic particles in said sample mixture, separated, and retained in the buffer liquid within the tube at the magnetizing station, are subsequently removed from the tube by terminating the introduction of said sample mixture into the buffer liquid, and the application of the magnetic field across the tube, while the buffer liquid is fed through the tube to flush out said magnetically-stained target particles with the buffer liquid.

4. The method according to claim 1, wherein said buffer liquid and sample mixture are gravity fed through said tube into a receiving container.

5. The method according to claim 4, wherein a vacuum is applied to said receiving container for controlling the feeding of said buffer liquid and sample mixture into said receiving container.

6. The method according to claim 4, wherein a positive pressure is applied to said tube to control the feeding of said buffer liquid and sample mixture into said receiving container.

7. The method according to claim 1, wherein said target particles are selected biological cells in said sample.

8. The method according to claim 7, wherein said sample is a blood sample, and said target cells are a selected type of lymphocyte in the blood sample.

9. The method according to claim 1, wherein said magnetic particles mixed with the sample are in the form of magnetic microbeads.

10. The method according to claim 1, wherein said magnetic field is controlled to produce a predetermined field intensity.

11. Apparatus for magnetically separating target particles of a selected type from a sample in order to produce a concentration of the target particles in the sample, or a depletion of the sample with respect to the target particles, comprising:

a buffer liquid supply;

a tube for feeding a buffer liquid from said buffer liquid supply at an inlet end of the tube to an outlet end of the tube;

a sample container for containing a mixture of said sample with magnetic particles having a selective affinity to magnetically stain said target particles;

a feed tube connecting said container to said inlet end of said tube to enable feeding said mixture through said tube after a flow of buffer liquid has been produced therein, such that the buffer liquid forms a continuous liquid carrier for the magnetically-stained target particles of the mixture fed through the tube;

magnetic field producing means for producing a magnetic field across the tube at a magnetizing station therein to cause the magnetically-stained target particles to be separated and retained in the buffer liquid within the tube at said magnetizing station;

and a container located at the outlet end of the tube for receiving the buffer liquid and the sample depleted of the target particles.

12. The apparatus according to claim 11, wherein said input port includes a first connection connecting the buffer liquid supply to the inlet end of the tube, and a second connection for introducing the sample mixture into said buffer liquid at a location between the said inlet end of the tube and said magnetizing station.

13. The apparatus according to claim 11, wherein said container is located below said inlet end of the tube such that the buffer liquid and sample mixture are gravity fed through said tube to said container.

14. The apparatus according to claim 13, wherein said container is connected to a suction source for controlling the feeding of the buffer liquid and sample mixture through the tube.

15. The apparatus according to claim 13, wherein said tube includes a positive pump to control the feeding of the buffer liquid and sample mixture through said tube.

16. The apparatus according to claim 11, wherein said apparatus further comprises a second container to be located at the outlet end of the tube in place of said first-mentioned container; and wherein both the application of the magnetic field, and the introduction of said sample mixture into the buffer liquid, are terminable to cause the buffer liquid being fed through the tube to flush-out the magnetically-stained target particles into said second container.

17. The apparatus according to claim 11, wherein said apparatus further comprises an air bubble sensor for sensing the presence of air in the buffer liquid fed through said tube, an air bubble sensor for sensing the presence of air in the sample mixture fed to said tube, and a controller controlled by said sensors for interrupting the flow of said buffer or sample mixture upon the detection of an air bubble therein.

18. The apparatus according to claim 11, wherein said magnetic field is produced by magnets mounted on magnetizable core elements defining a closed magnetic circuit including a first air gap between the magnets, and a second air gap between the magnetizable core elements; said tube passing through both said air gaps.

19. The apparatus according to claim 18, wherein said magnetizable core elements also define a third air gap, through which said tube also passes.

20. The apparatus according to claim 11, wherein said magnetic field producing means includes permanent magnets which are physically movable from the vicinity of the tube to terminate the application of the magnetic field across the tube at said magnetizing station.

21. The apparatus according to claim 11, wherein said magnetic field producing means includes an electromagnet which is electrically deenergisable to terminate the application of the magnetic field across the tube at said magnetizing station.

22. The apparatus according to claim 11, further including a control system for controlling the magnetic field to produce a predetermined field intensity.

* * * * *